Figure 1:
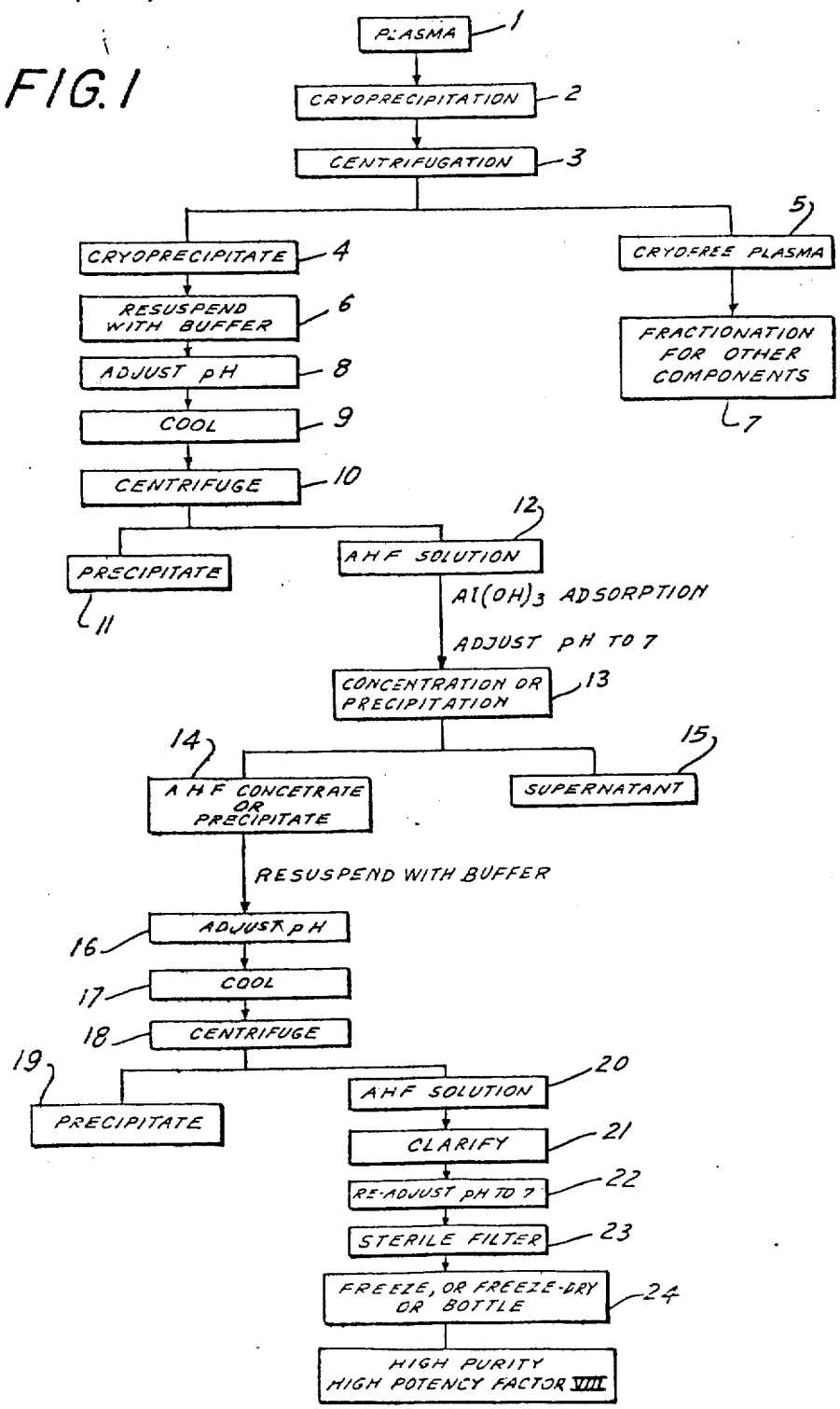

– – –

United States Patent [19]

Feldman

[11] 4,294,826
[45] Oct. 13, 1981

[54] PROCESS FOR THE PREPARATION OF HIGHLY PURIFIED ANTIHEMOPHILIC FACTOR

[75] Inventor: Fred Feldman, Park Forest, Ill.

[73] Assignee: Armour Pharmaceutical Company, Tuckahoe, N.Y.

[21] Appl. No.: 147,441

[22] Filed: May 7, 1980

[51] Int. Cl.³ .................... A61K 35/14; A61K 37/00
[52] U.S. Cl. ............................ 424/101; 260/112 R; 424/177
[58] Field of Search .................... 424/101, 177; 260/112 R

[56] References Cited

U.S. PATENT DOCUMENTS

| | | | |
|---|---|---|---|
| 3,973,002 | 8/1976 | Hagan et al. | 424/101 |
| 4,093,608 | 6/1978 | Iga et al. | 424/101 |
| 4,170,639 | 10/1979 | Liu et al. | 424/101 |

OTHER PUBLICATIONS

Nilsson et al., Scand. J. Haematol. vol. 24 (1980) pp. 340–349.

*Primary Examiner*—Sam Rosen
*Attorney, Agent, or Firm*—Ernest B. Lipscomb, III

[57] ABSTRACT

An antihemophilic factor derived from human blood plasma, having about 1 to 10 units antihemophilic factor activity per mg of protein and being substantially free of denatured antihemophilic factor is prepared from material having 0.3 to 1.0 unit per mg of protein.

4 Claims, No Drawings

PROCESS FOR THE PREPARATION OF HIGHLY PURIFIED ANTIHEMOPHILIC FACTOR

This invention relates to antihemophilic factor present in human blood plasma. It particularly relates to compositions containing antihemophilic factor (AHF) of high potency and purity and substantially free of denatured AHF and to processes for the preparation thereof.

The isolation of AHF by fractionation from other proteins present in blood plasma has been achieved. The prior art of AHF fractionation has demonstrated that AHF can be separated in part or in toto from fibrinogen and other proteins by column chromatography, polyethylene glycol (PEG) or polypropylene glycol (PPG) precipitation, glycine precipitation (or with other amino acids), as well as alcohol precipitation. British Patent No. 1,507,198 and U.S. Pat. No. 3,973,002 utilize pH and temperature adjustments to result in some purification of AHF, but the procedure described in these patents uses a starting material different from what is used in the process described in this application, and results in low potency preparations of intermediate purity. The processes described in these patents utilize a fraction extracted from the cryoprecipitate rather than cryoprecipitate itself. Furthermore, fractionation stops after one cycle of pH and cooling adjustment. Others have also recognized the effect of using one cycle of pH and cooling adjustment (J. K. Smith et al, Transfusion 19, 299–306, (1979)).

The compositions of AHF obtained by the prior art processes discussed above are of relatively low concentration (of the order of about 5 to 15 units of AHF activity per ml) and low purity (less than 1 unit AHF activity per mg protein), one of the undesirable impurities being denatured AHF.

It is, accordingly, an object of the present invention to provide an AHF composition of high potency and purity.

It is another object of the present invention to provide an AHF composition of high potency and purity and substantially free of denatured AHF.

It is a further object of the present invention to provide an improved process for preparing from aqueous compositions containing AHF obtained from human plasma, AHF compositions of high potency and purity and substantially free fo denatured AHF.

The present invention provides an aqueous composition of high concentration (about 20 to 45 units AHF activity per ml) and high potency (at least 1 unit AHF activity per mg of protein) and dried compositions having 1 to 10 units AHF per mg protein, such compositions being substantially free of denatured AHF, from human plasma by the process described below.

The process of the present invention may be applied to any aqueous composition of AHF having about 5 to 15 units AHF activity per ml, and a specific activity of about 0.3 to 1.0 unit AHF activity per mg of protein.

In accordance with the present invention such aqueous composition is subjected to the following steps:
 (a) effecting about a 2- to 10-fold concentration of the solution,
 (b) adjusting the pH of said concentrated solution to about 5.0 to 6.0,
 (c) cooling resultant solution to about 0° to 14° C.,
 (d) removing the precipitate which forms at said pH and temperature,
 (e) further clarifying the solution by filtration or other equivalent means, and
 (f) adjusting the pH to about 7.0.

The resulting solution is subjected to sterile filtration and the filtrate obtained therefrom may be put directly into sterile vials or freeze-dried to form a sterile dry preparation. The solutions and dry preparations may be marketed directly as such.

The present invention will be illustrated in the description which follows, with reference to FIG. 1 which is a flow sheet illustrating steps of a prior art process and the steps of the process of the present invention. This description is given by way of illustration and is not to be considered as limiting.

Human plasma is subjected to freezing, thawing, and centrifugation resulting in the removal of the cryoprecipitate. At physiological pH and temperature (pH 7–7.4, room temperature to 37° C.), the cryoprecipitate (#4) can be dissolved in a buffer (such as tris hydrochloride or glycine with saline and sodium citrate) to give a uniform solution. The cryoprecipitate, or a concentrated fraction from the cryoprecipitate contains a complex mixture of clotting proteins (including AHF), fibrinogen, albumin, and other proteins. By acidifying the resuspended cryoprecipitate (#6) (to a pH 6.0–6.8) (step #8) and cooling (to 15°–15° C.) (step #9) some of the proteins (such as the fibrinogen and the cold-insoluble globulins can be made to precipitate (step #10). By carefully choosing the right conditions, as described above (pH 6–6.8, temperature 5°–15° C.), AHF can be made to remain in the supernatant (step #12).

If the pH is made more acidic than pH 6.4 and the solution cooled at this step, (steps 8-12), more proteins are precipitated and can be removed from the solution, but AHF is also precipitated resulting in no additional purification. The processes described in the prior art do not go beyond this stage, and this has led to the assumption that further purification is not possible by the continued manipulation of pH and temperature.

In accordance with the present invention a high purity concentrate of AHF is obtained by the additional steps described below, reference, as noted above, being made to the flow sheet in FIG. 1.

The separated AHF solution (#12) after Al(OH)$_3$ absorbtion is concentrated or precipitated. The concentrated AHF solution (#14) has high potency (25–45 units per ml), but intermediate purity (less than one AHF unit per mg protein). The concentrated AHF solution (#14) (or concentrated resuspended AHF solution (#14) is then adjusted to pH 5.0–6.0 and cooled to 0°–14° C. at which temperature a precipitate forms. The precipitate (#19) is removed and the AHF (#20) solution clarified, adjusted to pH 7, sterile filtered and bottled or bottled and freeze-dried.

The sterile solution contains about 25 to 45 units per ml, has a potency of about 1 to 10 units AHF activity per mg of protein and is substantially free of denatured AHF.

The freeze-dried preparation contains about 1 to 10 units AHF activity per mg protein and is also substantially free of denatured AHF.

The present invention teaches, therefore, that if the AHF solution from the acidified and cooled steps (steps 8-12) is readjusted to pH 7 and concentrated, that subsequent acidification and cooling effect the removal by precipitation of additional large amounts of fibrinogen, plasminogen and plasmin, cold insoluble globulins, and other proteins without coprecipitation of AHF, and result in a gentle coversion from an intermediate potency intermediate purity AHF preparation to a high potency high purity preparation.

Attempting to extend the first acidification and cooling (steps 8-12) without this sequence is fruitless.

An additional benefit of this purification is that it is a gentle procedure and results in an AHF preparation which is native, that is, one in which the ratio of antigenic Factor VIII (FVIII Coagulant Antigen) to Factor VIII procoagulant activity is approximately one, indicating the absence of denatured AHF (one which shows substantial levels of inactive antigenic Factor VIII). No other purification scheme has been demonstrated to produce this unique result.

I claim:

1. A process for the preparation of an aqueous composition of antihemophilic factor having a concentration of about 20 to 45 units of antihemophilic factor per ml, a specific antihemophilic factor activity of at least 1 unit per mg protein, and being obtained from an aqueous solution of antihemophilic factor derived from human blood plasma, said aqueous solution having a concentration of about 5 to 15 units of antihemophilic factor per ml, and a specific antihemophilic factor activity of about 0.3 to 1.0 unit per mg protein, which comprises:

(a) effecting about a 2- to 10-fold concentration of the low concentrate solution, (b) adjusting the pH of said concentrated solution to about 5.0 to 6.0, (c) cooling the resultant solution to about 0° to 14° C., (d) removing the precipitate which forms at said pH and temperature, (e) further clarifying the solution from step (d), and (f) adjusting the pH to about 7.0.

2. An aqueous composition of antihemophilic factor derived from human blood plasma, said composition having a cencentration of 20 to 45 units of antihemophilic factor per ml, said antihemophilic factor having a specific antihemophilic factor activity of at least 1 unit per mg protein, when prepared by a process according to claim 1.

3. A freeze-dried composition of antihemophilic factor derived from human blood plasma, having about 1 to 10 units antihemophilic factor activity per mg protein with a ratio of antigenic Factor VIII to Factor VIII procoagulant activity of approximately one and being substantially free of denatured antihemophilic factor.

4. An aqueous composition of antihemophilic factor derived from human blood plasma, having a concentration of about 20 to 45 units antihemophilic factor activity per ml and at least 1 unit antihemophilic factor activity per mg protein, with a ratio of antigenic Factor VIII to Factor VIII procoagulant activity of approximately one and being substantially free of denatured antihemophilic factor.

* * * * *

UNITED STATES PATENT AND TRADEMARK OFFICE
CERTIFICATE OF CORRECTION

PATENT NO. : 4,294,826

DATED : October 13, 1981

INVENTOR(S) : Fred Feldman

It is certified that error appears in the above-identified patent and that said Letters Patent is hereby corrected as shown below:

Figure 1 of the drawing should be inserted as per attached attached sheet.

On the title page, delete "No Drawings" and substitute therefor -- 1 Drawing Figure --.

Signed and Sealed this

Nineteenth Day of April 1983

[SEAL]

Attest:

Attesting Officer

GERALD J. MOSSINGHOFF

Commissioner of Patents and Trademarks